United States Patent [19]
Lary

[11] Patent Number: 5,372,601
[45] Date of Patent: Dec. 13, 1994

[54] LONGITUDINAL RECIPROCATING INCISOR

[76] Inventor: Banning G. Lary, 6271 SW. 87th Ter., Miami, Fla. 33143

[21] Appl. No.: 39,881

[22] Filed: Mar. 30, 1993

[51] Int. Cl.$^5$ .............................................. A61B 17/32
[52] U.S. Cl. ..................................... 606/159; 606/171
[58] Field of Search ............... 606/166, 167, 159, 170, 606/171, 180; 30/151; 604/22, 54, 96

[56] References Cited

U.S. PATENT DOCUMENTS

| | | |
|---|---|---|
| 2,505,358 | 4/1950 | Gusberg . |
| 3,837,345 | 9/1974 | Matar . |
| 4,273,128 | 6/1981 | Lary . |
| 4,589,412 | 5/1986 | Kensey . |
| 4,627,436 | 12/1986 | Leckrone . |
| 4,895,166 | 1/1990 | Farr et al. . |
| 5,053,044 | 10/1991 | Mueller et al. ........................ 606/159 |
| 5,092,872 | 3/1992 | Segalowitz ........................... 606/159 |
| 5,224,949 | 7/1993 | Gomringer et al. ................. 606/170 |
| 5,242,461 | 9/1993 | Kortenbach et al. ............... 606/159 |

FOREIGN PATENT DOCUMENTS 2044103A 3/1979 United Kingdom ......... A61B 17/22

Primary Examiner—Stephen C. Pellegrino
Assistant Examiner—William W. Lewis
Attorney, Agent, or Firm—Nydegger & Associates

[57] ABSTRACT

An medical instrument which is insertable into an arterial system to incise an arterial stenosis is provided and includes a cutting member selectively covered by a catheter sheath. The sheath is shaped to provide protection against unintentional incisions during insertion and placement of the device. Longitudinal slots are formed by the body of the sheath and are engaged by alignment lugs included on the cutting member such that the interaction between the slots and the lugs provides the surgeon with added control over the length of the incisions. In operation, the device is placed next to a stenosis and the cutting member is advanced relative to the sheath to longitudinally incise the stenosis. After incising the stenotic segment, an inflatable balloon included on the device is placed in the stenotic segment and standard dilation is performed.

23 Claims, 3 Drawing Sheets

LONGITUDINAL RECIPROCATING INCISOR

TECHNICAL FIELD

The present invention pertains generally to medical devices for reducing the flow restriction caused by a stenosis in an artery. More specifically, the present invention relates to devices for incising an arterial stenosis. The present invention is particularly, but not exclusively, useful for longitudinally incising an arterial stenosis prior to and in conjunction with angioplasty.

BACKGROUND OF THE INVENTION

It is well known that any significant reduction or restriction in the flow of blood through the arteries of the body can cause complications which may have serious consequences. Arterial blockages caused by plaque and fibrosis build-up in the arteries are known to be a leading cause of heart attacks, strokes, and other debilitating maladies. Accordingly, it is extremely important for the health of a patient that any stenosis, or blockage, which is causing such a condition, be eliminated or reduced.

Fortunately, with the advent of so-called bypass surgery techniques, the consequences of blockages in various arteries can be alleviated by grafting replacement arterial tissue to the affected artery. In this manner, blood is allowed to bypass the blockage in the affected artery and the blood supply to the body tissue which is downstream from the blockage is thereby restored. While bypass surgical procedures have become relatively safe, reliable, and effective, portions of the body must nevertheless be opened to accomplish the surgery. In other words, bypass surgery is invasive, and can consequently require significant post-operative recovery time. To avoid the drawbacks associated with invasive bypass surgery, less invasive surgical procedures have been developed wherein a device is inserted into the bloodstream of a patient and advanced into an artery to reduce or remove an arterial stenosis.

One well known and frequently used procedure to accomplish this task is popularly known as angioplasty. For a basic angioplasty procedure, a dilating balloon is positioned across the particular stenotic segment and the balloon is inflated to open the artery by breaking up and compressing the plaque which is creating the stenosis. The plaque, however, remains in the artery and is not removed. Unfortunately, in some cases, it appears that the plaque which remains in the artery may still present a stenosis. Furthermore, in approximately 30–60% of the vessels treated by angioplasty, there is a re-stenosis. This high recurrence rate is thought to be the result of fibrotic contraction in the lumen of the vessel. In these situations, other more drastic procedures need to be employed.

As an alternative to angioplasty, atherectomy procedures have been developed to resolve the problems caused by blocked arteries. However, unlike an angioplasty procedure which opens the stenosis in the artery but does not remove the plaque which caused the stenosis, an atherectomy procedure mechanically cuts and removes the plaque which is creating the stenosis from the artery. Many examples of such cutting devices can be given. For instance, U.S. Pat. No. 4,895,166 which issued to Farr et al. for an invention entitled "Rotatable Cutter for the Lumen of a Blood Vessel", and which is assigned to the same assignee as the present invention, discloses such a cutter. U.S. Pat. No. 4,589,412 which issued to Kensey for an invention entitled "Method and Apparatus for Surgically Removing Remote Deposits" is but another example.

Fixed atherectomy devices are typically limited to producing cutting paths having diameters less than or approximately equal to the insertion diameter of the devices. Accordingly, expandable cutting atherectomy devices have been developed which allow cutting paths having diameters greater than the insertion diameter of the devices. Examples are disclosed in U.S. Pat. No. 4,966,604 which issued toe Reiss for an invention entitled "Expandable Atherectomy Cutter with Flexibly Bowed Blades", and U.S. Pat. No. 4,986,807 which issued to Farr for an invention entitled "Atherectomy Cutter with Radially Projecting Blade", both of which patents are assigned to the same assignee as the present invention. These devices expand their cutting surfaces after insertion into the vessel to be cleared.

A common characteristic of the foregoing fixed and expandable atherectomy devices is that they all produce cuttings from the stenosis which must be collected and removed from the artery. This collection of cuttings is necessary to prevent the cuttings from forming another blood vessel blockage. Angioplasty procedures, however produce no cuttings and correspondingly do not require cutting collection. Unfortunately, standard angioplasty sometimes results in only a small opening through the stenotic segment of the artery. To overcome this problem, improved angioplasty procedures have been developed which do not produce loose cuttings from the stenosis while they do increase the diameter of the stenotic segment passage beyond the diameter produced by simple angioplasty. One such procedure is disclosed in U.S Pat. No. 4,273,128 which issued to the inventer of the present invention for an invention entitled "Coronary Cutting and Dilating Instrument". According to this procedure, a catheter based device is used to make longitudinal cuts in a stenotic segment of an artery prior to angloplastic enlargement of the segment.

It has been shown that when an angioplasty procedure is performed after the stenotic segment is longitudinally incised, the opening established through the segment is much larger as compared to standard angioplasty without the prior incisions. Still further, the increase in the opening in the stenotic segment is accomplished without the production of cuttings like those resulting from atherectomy procedures and without tearing the vessel wall. Moreover, it has been found that incising the stenosis prior to dilation allows greater compression of the stenotic tissue with decreased likelihood of the stenosis rebuilding at a later date. As those skilled in the art will appreciate, the plaque creating a common arterial stenosis is somewhat fibrous and will tend to return to its original predilation configuration. With this fibrous composition, the stenosis is therefore more likely to maintain a compressed configuration if the fibers are incised prior to balloon dilation. On the other hand, if the fibers in the stenosis is not incised first, the completeness of the compression of the stenosis is dependant on whether the inflated balloon is able to break apart fibers in the tissue. As those skilled in the art will recognize, dilation of a segment is of course limited by the arteries able to withstand dilation. Over-dilation can have the catastrophic result of rupturing the vessel.

While a procedure involving incision before dilation is typically effective, flexibility of the shaft connected to the cutting member can result in diminished surgical control over the cutting member. More specifically, control over the orientation and magnitude of travel of the cutting element is hampered by torsional and longitudinal flexibility of the connecting shaft. For example, a surgeon may want to make a 0.5 cm incision, but, the inherent flexibility of the shaft may result in incisions which are shorter than desired.

In light of the above, it is an object of the present invention to provide an improved device and method for longitudinally incising a stenotic segment of an artery prior to an angioplasty procedure. It is another object of the present invention to provide a cutting device which, in cooperation with an angioplasty procedure, is able to produce an opening in a stenotic segment where the diameter of the opening is greater than the insertion diameter of the device. It is yet another object of the present invention to provide a device insertable into an obstructed artery which incises a stenosis without producing potentially harmful cuttings. It is also an object of the present invention to provide a device which allows improved control over the length of the incisions produced in the stenotic segment. Yet another object of the present invention is to provide a device which is flexible enough to allow advancement of the device through narrow vessels and around sharp turns. Still further, it is an object of the present invention to provide a device for longitudinally incising a stenotic segment of an artery which is relatively easy to manufacture and is comparatively economical.

SUMMARY OF THE INVENTION

The present invention is an insertable catheter device which longitudinally incises a stenotic segment of an artery prior to balloon dilation. Generally, the catheter device includes a hollow catheter sheath and a cutting member which is reciprocatably mounted in the catheter sheath.

More specifically, the cutting member includes a central hollow shaft having a lumen which is sized to be placed on a typical guide wire. Attached near the distal end of the shaft are one or more cutting units, such as cutting blades or cauteries, which extend radially from the shaft.

The hollow catheter sheath is formed with an opening at its distal end which includes a circular center having a diameter sufficient to allow the guide wire and the hollow shaft of the cutting member to extend therethrough. The opening also includes one or more longitudinally aligned slots which extend radially from the circular center. As intended for the present invention, the cutting member is normally enclosed in the catheter sheath and is reciprocatingly disposed therein to be selectively extended from the sheath as desired by the operator. To permit this change in configuration, the slots at the end of the catheter sheath are sized to allow the cutting units attached to the shaft to exit the sheath whenever the cutting member is moved distally relative to the sheath. Thus, while the sheath can cover the cutting member during insertion and placement of the device (the insertion configuration), the cutting member can also be advanced relative to the sheath (the cutting configuration) to make incisions in the stenotic segment. In this, the cutting configuration, the portion of the hollow shaft including the cutting units extends out of the distal end of the sheath allowing the cutting units to incise the stenosis.

To facilitate insertion and placement, the distal end of the sheath is tapered to a rounded point. Moreover, the wall thickness of the sheath is increased near the distal end to prevent the distal end from enlarging and splaying during insertion and placement of the device.

Attached to the hollow shaft of the cutting member, at a location proximal of the cutting units, are a plurality of lugs. These lugs are equally spaced about and radially extend from the hollow shaft. Additionally, the lugs radially extend a sufficient distance to cooperatively engage longitudinal slots which are formed in the inside wall of the catheter sheath. The engagement between the lugs and the longitudinal slots allows the shaft to reciprocate a predetermined distance while preventing rotation of the shaft relative to the sheath. In this manner the longitudinal slots in the catheter sheath determine the maximum length of the incisions in the stenotic segment while maintaining the alignment of the cutting member relative to the sheath.

While the device of the present invention can be used and removed prior to a standard angioplasty procedure, it is likewise possible for the device to include an inflatable balloon along the hollow shaft between the cutting member and the lugs. The device can then be used to create the longitudinal incisions in the stenotic segment as well as perform the angioplasty procedure.

The shaft of the cutting member is typically relatively rigid. Alternatively, when it is desirable to incise a stenosis located in a bend in a vessel, the shaft can include a flexible portion.

To use the device of the present invention, a standard guide wire is placed into the arterial system of a patient and passed through the stenotic segment. The device of the present invention is placed on the guide wire and then advanced through the arterial system, along the guide wire, until it is located adjacent the stenosis. With the device in place, the surgeon passes the cutting units through the stenotic segment by advancing the hollow shaft relative to the catheter sheath thereby incising the stenosis. Having passed the cutting units through the segment, the shaft is then retracted relative to the sheath. It is possible that multiple passes will be desirable to produce a greater number of incisions. If this is the case, the sheath, and therefore the cutting member, can be rotated slightly between successive passes through the stenotic segment.

After having made sufficient longitudinal incisions in the stenotic segment, the shaft can be advanced an amount sufficient to place the inflatable balloon in the stenotic segment. The balloon can then be inflated and deflated to compress the stenotic tissue and expand the opening through the stenosis. Alternatively, the device can be removed from the arterial system and a standard angioplasty procedure can be performed on the incised stenosis.

BRIEF DESCRIPTION OF THE DRAWINGS

The novel features of this invention, as well as the invention itself, both as to its structure and its operation will be best understood from the accompanying drawings, taken in conjunction with the accompanying description, in which similar reference characters refer to similar parts, and in which.

DESCRIPTION OF PREFERRED EMBODIMENTS

Figure 1:
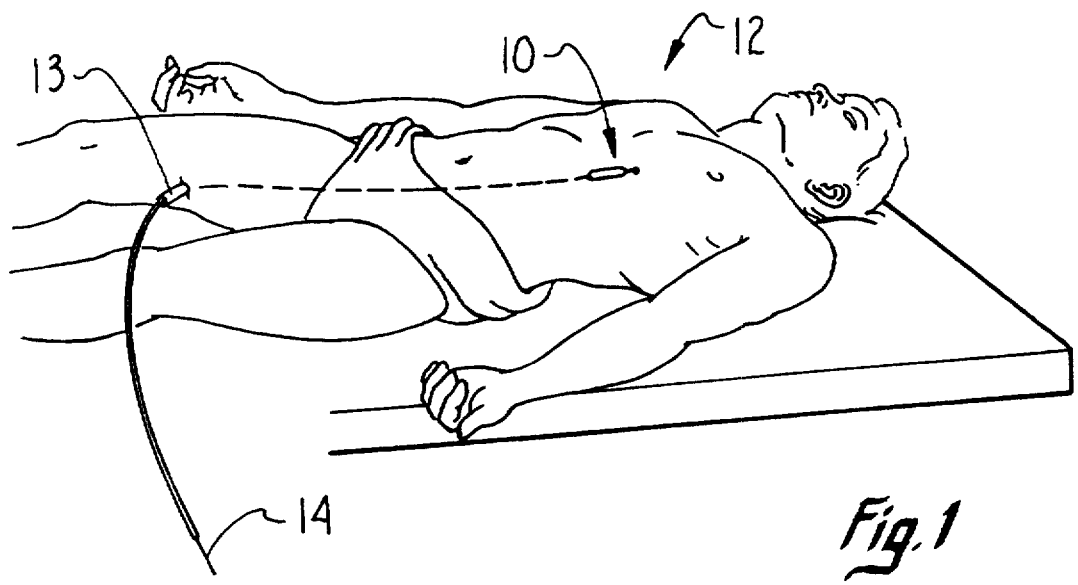
FIG. 1 is a perspective view of a patient having the device of the present invention inserted into his arterial system.

Referring initially to FIG. 1, the longitudinal cutting device of the present invention is shown and generally designated 10. Device 10 is shown inserted into the arterial system of a man 12 in the customary manner. Typically, device 10 is inserted through an insertion catheter 13 into the femoral artery and advanced through the arterial system to the stenotic segment.

Figure 2:
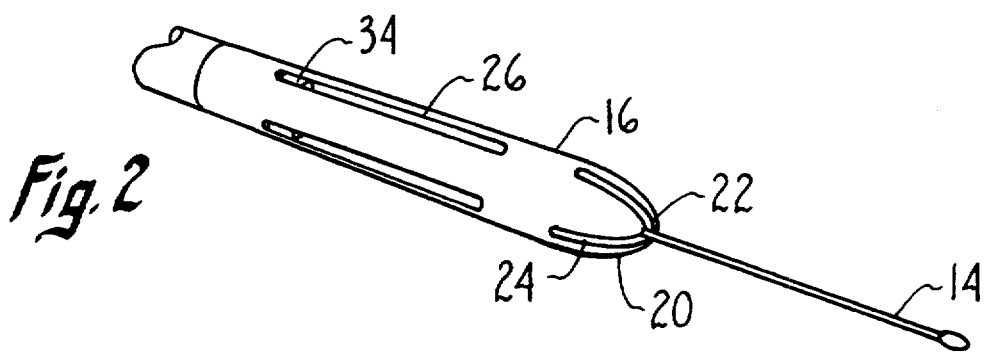
FIG. 2 is a perspective view of the device of the present invention in the insertion configuration.
Figure 3:
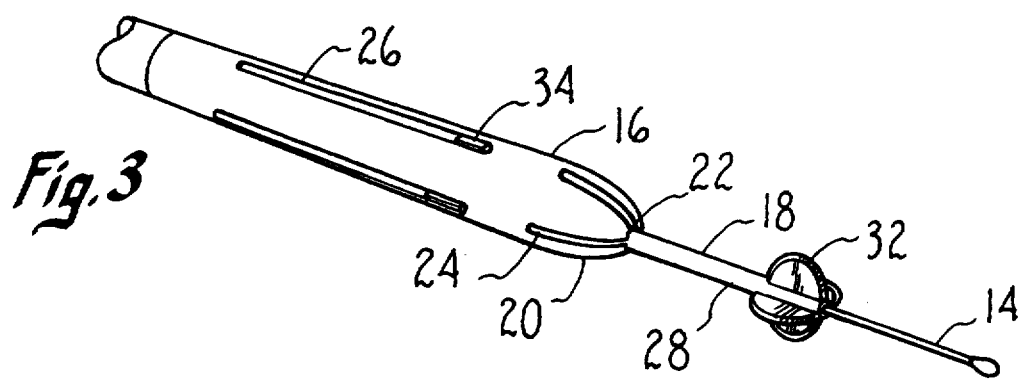
FIG. 3 is a perspective view of the device of the present invention in the cutting configuration.

Referring now to FIGS. 2 and 3, device 10 is shown on a standard guide wire 14. Generally the device 10 includes a catheter sheath 16 and a cutting member 18. FIG. 2 shows the insertion configuration of device 10 wherein the cutting member 18 is retracted into the catheter sheath 16. FIG. 3 shows the extended or cutting configuration of device 10 wherein the cutting member 18 extends from the distal end 20 of the catheter sheath 16. Catheter sheath 16 is formed with an opening 22 at its distal end which allows both the guide wire 14 and the cutting member 18 to exit. Opening 22 includes radial slots 24 extending from a substantially circular center portion. The hollow interior of sheath 16 and opening 22 are formed to provide a means for receiving and enclosing the cutting member 18. Catheter sheath 16 also forms longitudinal slots 26 located more proximally along the body portion of the sheath.

Figure 4:
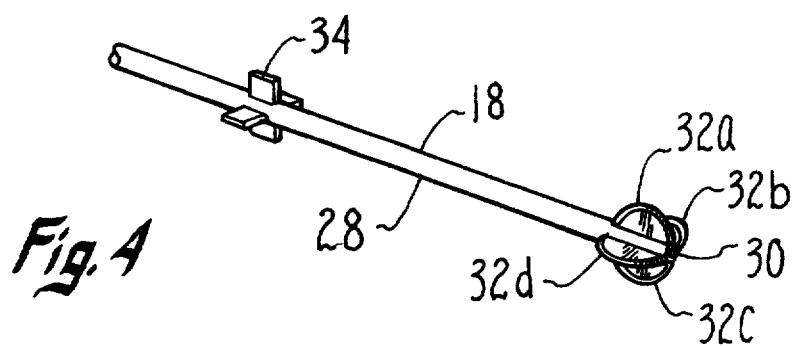
FIG. 4 is a perspective view of the cutting member of the present invention.

Referring now to FIG. 4, the cutting member 18 is shown and including a hollow shaft 28 defining a lumen 30. Lumen 30 is of sufficient size to accommodate a standard guide wire and to act as a fluid conduit for dilating an angioplastic balloon. Dilation fluid is prevented from exiting the end of hollow shaft 28 by a seal (not shown) in the lumen of the shaft. As will be appreciated by those skilled in the art, shaft 28 may be solid if a guide wire is not required.

Cutting blades 32 are attached to shaft 28 at its distal end and extend radially from and are symmetrical about shaft 28. While four blades 32a-d are shown, it is to be appreciated that one or more blades could be used. Moreover, as can be appreciated by those skilled in the art, cutting blades 32 could be replaced by cauteries or lasers. The number of radial slots 24 in distal end 20 corresponds to the number of blades or cauteries.

Alignment lugs 34 are also attached to shaft 28, although at a location more proximal than the cutting blades 32. While four, radial, symmetrically spaced lugs 34 are shown, one or more lugs could be used without departing from the scope of the present invention.

Figure 5:
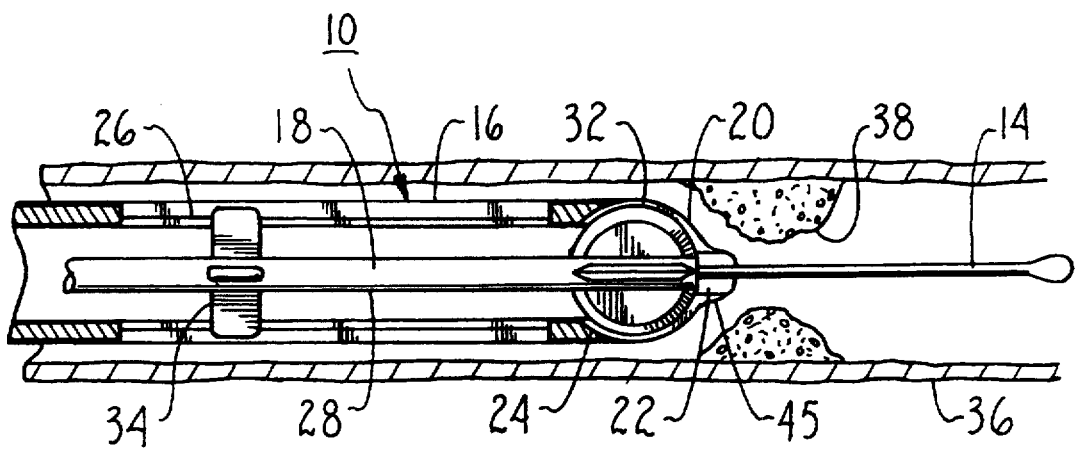
FIG. 5 is a cutaway view of the device of the present invention in the insertion configuration and adjacent a stenotic segment of an artery.
Figure 6:
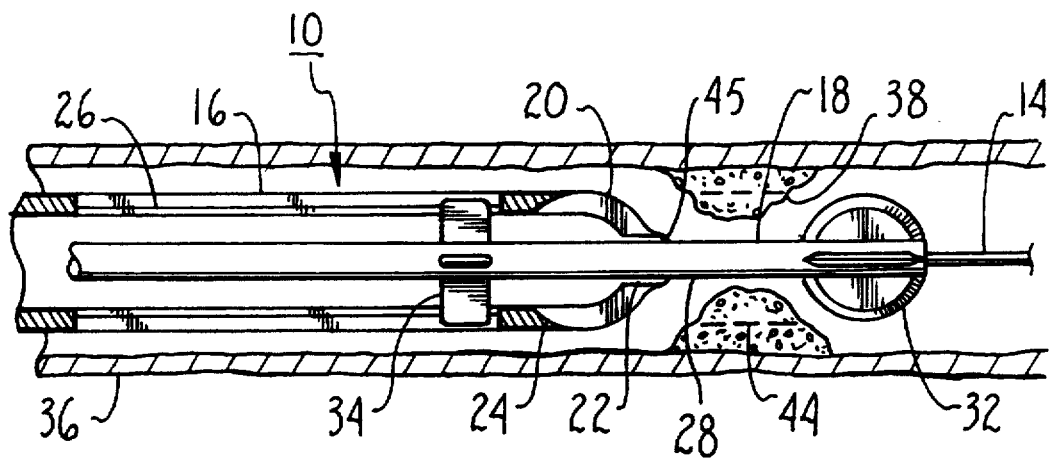
FIG. 6 is a cutaway view of the device of the present invention in the cutting configuration where the cutting member has incised the stenotic segment.

Referring now to FIGS. 5 and 6, the cooperation between the catheter sheath 16 and the cutting member 18 can be more clearly seen. Device 10 is shown installed on a guide wire 14 and in an artery 36 adjacent a stenosis 38. In FIG. 5, device 10 is in the insertion configuration where cutting member 18 is retracted into the radial slots 24 of catheter sheath 16. In this configuration, the cutting blades 32 are prevented from contacting the artery wall and making unintentional incisions during insertion and placement. Alignment lugs 34 slidingly engage longitudinal slots 26. The cooperative engagement between the lugs 34 and the longitudinal slots 26 allows cutting member 18 to move longitudinally a predetermined distance, but prevents cutting member 18 from rotating relative to the sheath 16. In this manner, blades 32 are maintained in alignment with radial slots 24 and longitudinal travel of cutting member 18 is limited by the length of longitudinal slots 26. While longitudinal slots 26 are shown as extending from the inside wall of sheath 16 to the outside of sheath 16, it is possible to use slots not completely passing through the sheath wall without departing from the scope of the present invention. It is to be appreciated that by having slots 26 completely pass through the wall of sheath 16, the blood flow restriction caused by the instrument is reduced. Said differently, by including through slots 26, blood can flow through the slots 26, the sheath 16 and radial slots 24 to reduce the flow restriction caused by the instrument itself.

FIG. 6 shows device 10 in the extended or cutting configuration where cutting member 18 is extending from the catheter sheath 16. Alignment lugs 34 remain in the longitudinal slots 26 at all times during the reciprocating movement of the cutting member 18 relative to the catheter sheath 16. The distal end 20 of catheter sheath 16 is tapered to a rounded point 45 to facilitate insertion and placement of the device 10. Moreover, the catheter sheath wall thickness at distal end 20 is increased to prevent the end from enlarging or splaying during insertion and placement of device 10.

Figure 7:
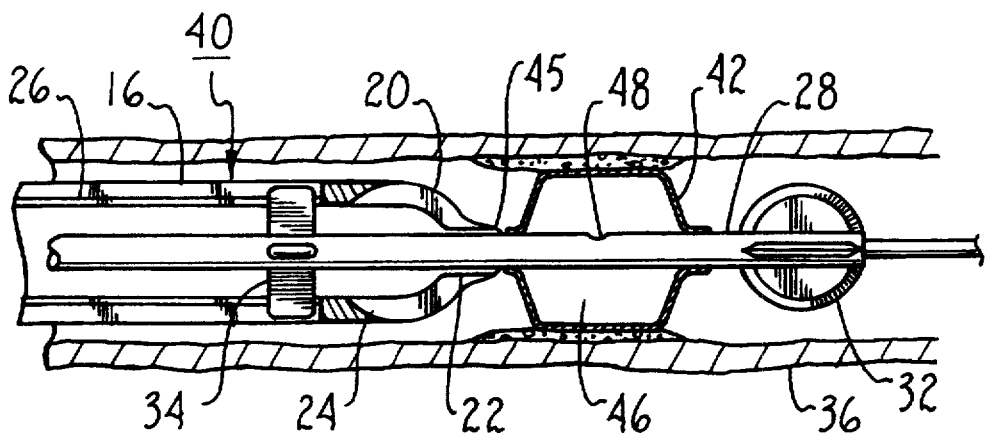
FIG. 7 is a cutaway view of an alternative embodiment of the device of the present invention including an inflatable angioplasty balloon where the balloon is inflated to enlarge the opening in the stenotic segment.

Referring to FIG. 7, an alternative embodiment of the present invention is shown and generally designated 40. This embodiment has a catheter sheath 16, a cutting member 18 having cutting blades 32 and alignment lugs 34, as well as longitudinal slots 26 and radial slots 24. The difference between device 40 and device 10 is that device 40 includes an inflatable dilation balloon 42 attached to the cutting member 18 between the cutting blades 32 and the alignment lugs 34. The dilation balloon 42 is well known and as those skilled in the art will appreciate, the location of balloon 42 in device 40 can be varied to accommodate the procedure for which it is to be used. For example, in some situations it may be desirable to place the dilation balloon distally of the cutting blades 32. In the depicted embodiment, the interior 46 of the dilation balloon 42 is connected to a balloon inflation means via the lumen 30 and fluid opening 48 as is well known in the art.

Figure 8:
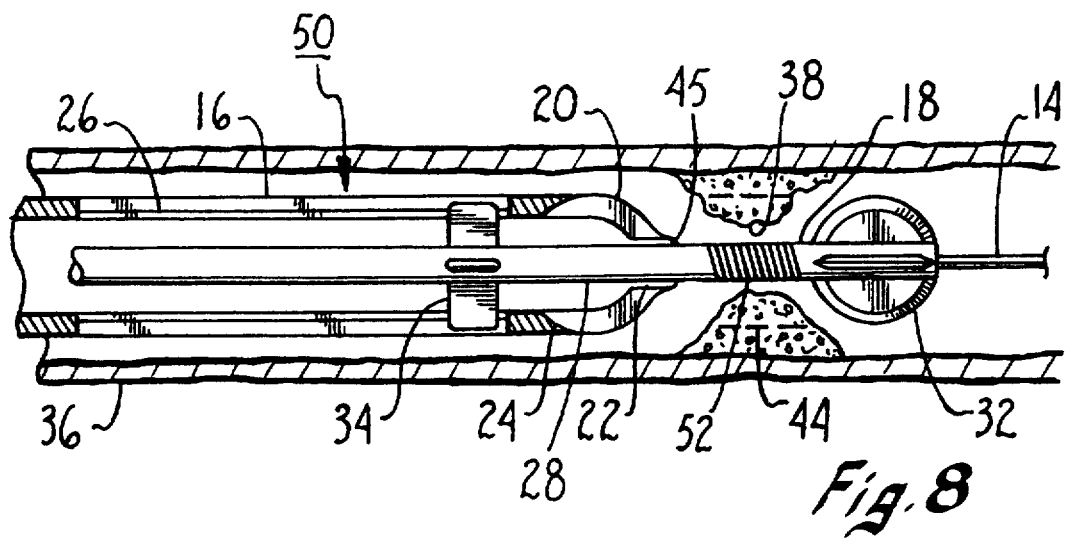
FIG. 8 is a cutaway view of an alternate embodiment of the device of the present invention including the flexible shaft and in the cutting configuration where the cutting member has incised the stenotic segment.

Referring now to FIG. 8, an alternative embodiment is shown and generally designated 50. Device 50 is substantially the same as device 10 except that shaft 28 includes a flexible member 52. As those skilled in the art will appreciate, flexible member 52 can be a coiled spring, such as is used in a flexible guide wire, as well as any other material allowing localized bending of shaft 28. Additional flexible members could be added along shaft 28 to provide additional flexibility. One of the reasons for including the flexible member 52 is to permit shaft 28 to follow the path of the flexible guide wire 14 through the curves and branches of the coronary artery tree. Inclusion of one or more flexible members 52 allows device 50 to be used in situations where the stenotic segment is located at or near a bend in the vessel. In those situations, it may be necessary for the incisions to be made along an axis noncolinear with the longitudinal axis of device 50. Flexible member 52 allows the necessary flexibility to achieve this noncolinear incising.

Figure 9:
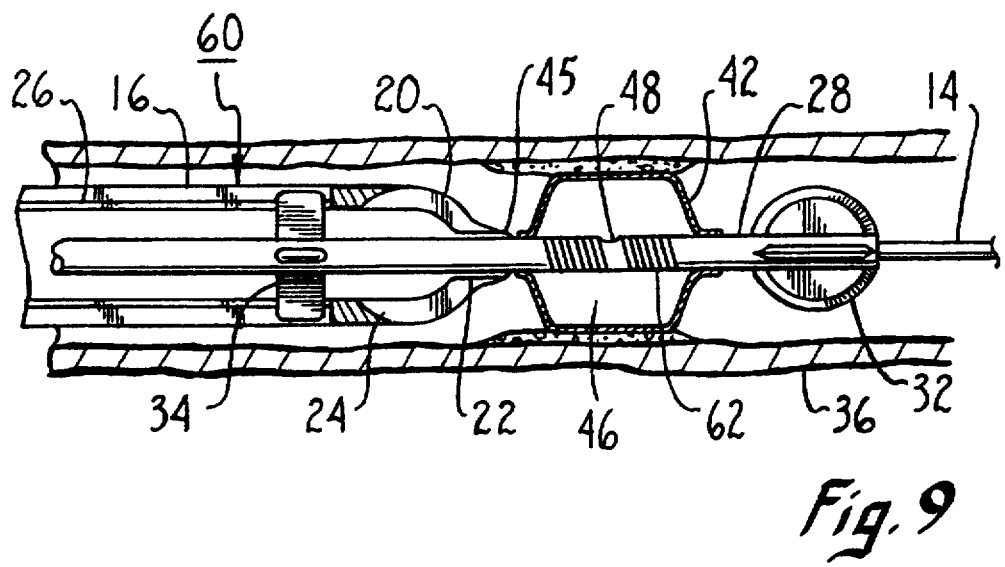
FIG. 9 is a cutaway view of an alternative embodiment of the device of the present invention including the flexible shaft and an inflatable angioplasty balloon where the balloon is inflated to enlarge the opening in the stenotic segment.

Referring now to FIG. 9, yet another alternative embodiment is shown and generally designated 60. Device 60 is substantially the same as device 40 except that shaft 28 includes a flexible member 62. While FIG. 9 shows a flexible member on either side of fluid opening 48, it is to be appreciated that a single flexible member 62 on only one side of fluid opening 48 would not depart from the scope of the present invention. Flexible member 62 allows shaft 28 to flex when it is desirable to have incisions noncolinear with the longitudinal axis of device 60. As those skilled in the art will appreciate, it may be desirable to provide additional flexible members 62 to provide additional flexibility. Additional flexible members 62 can be located within the balloon or outside the balloon along shaft 28.

OPERATION

To use the device of the present invention, device 10 is typically inserted into the arterial system through an insertion catheter 13 previously inserted into the femoral artery as shown in FIG. 1. When inserted, device 10 is in the insertion configuration as is depicted in FIGS. 2 and 5 where the cutting member 18 is retracted into catheter sheath 16. Device 10 is advanced into the artery 36 having a stenotic segment and is positioned adjacent the stenosis 38 as is well known in the art. Once adjacent the stenotic segment, cutting member 18 is advanced distally while the catheter sheath 16 is held stationary. In this manner, cutting blades 32 exit catheter sheath 16 and make incisions 44 in stenosis 38 as shown in FIG. 6. If being used in the coronary artery system, the cutting action of the device is increased by the contractions of the heart itself. Each time the muscles adjacent the stenotic segment of the artery contract, the stenosis is forced against the cutting surfaces of the instrument. Similarly, when the muscle relaxes, the stenosis can move away from the cutters. In effect, the contractions and relaxations provide a chopping or sawing action which in turn increases the effectiveness of the cutters.

Another way to increase the cutting action of the device is to manually or mechanically move the shaft 28, and therefore the cutters, in a "to-and-fro" motion as the blades 32 are passed through the stenotic segment. This sawing action, as noted above, results in increased cutting efficiencies. After making incisions 44, cutting member 18 can be retracted.

In some situations, a single incisional pass through the stenotic segment may be sufficient, although typically it will be preferable to increase the number of incisions using multiple passes. To make the additional incisions, the catheter sheath 16 is rotated slightly between passes through the stenosis 38. Rotating the sheath 16 rotates cutting blades 32 because the cutting member 18 is held in rotational alignment with sheath 16 by the cooperation between lugs 34 and longitudinal slots 26.

Surgical control over the length of the incisions is also provided by the device of the present invention. In the present device, the maximum length of an incision is determined by the length of the longitudinal slots 26. As long as the catheter sheath 16 is maintained in a constant position, the surgeon knows the exact length of incision which is possible, and the risk of incising the artery beyond the stenosis is reduced.

Once the incisions have been made, the stenosis is ready to be dilated. Dilation can be accomplished by positioning and inflating an inflatable balloon connected to the device of the present invention as is shown in FIG. 7. Alternatively, device 10 can be removed from the arterial system and a routine angioplasty procedure can be performed using the same guide wire.

It is worth noting that for long stenoses, the catheter can be advanced after the incisions have been made. In this manner, the catheter acts as a dilator. Accordingly, by alternatingly incising and advancing the catheter, very long stenoses can be treated. Because the distal end of the catheter is rounded, dilation using the catheter is possible with minimal risk of damaging the artery. The risk of arterial damage would be significantly greater using a standard catheter which did not include a rounded distal end.

While the particular longitudinal reciprocating incisor as herein shown and disclosed in detail is fully capable of obtaining the objects and providing the advantages herein before stated, it is to be understood that it is are merely illustrative of the presently preferred embodiments of the invention and that no limitations are intended to the details of construction or design herein shown other than as described in the appended claims.

What is claimed is:

1. A device insertable into an artery for cutting stenotic tissue comprising:
   a catheter sheath including a body portion, a proximal end and a distal end, said sheath defining a longitudinal axis and an internal receiving means at said distal end, said body portion having an inner surface and an outer surface;
   a cutting member for incising tissue comprising a shaft supporting cutting means, said cutting member being reciprocatable along said longitudinal axis, said cutting member being located entirely within said receiving means when in a retracted position and partially extending out of said receiving means when in an extended position; and
   restricting means included in said catheter sheath for limiting and aligning reciprocations of said cutting member, said restricting means engaging said cutting member to prevent rotation of said cutting member relative to said sheath.

2. The device as recited in claim 1 wherein said receiving means prevents said cutting means from contacting said tissue when said cutting member is in said retracted position.

3. The device as recited in claim 2 wherein said receiving means comprises an internal coaxial void defined by said inner surface, and an opening formed by said distal end of said sheath, said opening being shaped and sized to allow said cutting means to exit said coaxial void.

4. A device insertable into an artery for cutting stenotic tissue comprising:

a catheter sheath including a body portion, a proximal end and a distal end, said sheath defining a longitudinal axis and an internal receiving means at said distal end, said body portion having an inner surface and an outer surface;

a cutting member for incising tissue comprising a shaft supporting cutting means, said cutting member being reciprocatable along said longitudinal axis, said cutting member being located entirely within said receiving means when in a retracted position and partially extending out of said receiving means when in an extended position;

restricting means included in said catheter sheath for limiting and aligning reciprocations of said cutting member, said restricting means engaging said cutting member; and a plurality of alignment lugs radially extending from and attached to said shaft proximally of said cutting means, said alignment lugs slidingly engaging said restricting means to limit and align said reciprocations of said cutting member.

5. The device as recited in claim 4 wherein said restricting means is a plurality of longitudinal slots formed by said inner surface of said sheath.

6. The device as recited in claim 1 wherein said cutting means comprises at least one cutting blade attached to and radially extending from said shaft.

7. The device as recited in claim 1 wherein said cutting means comprises a plurality of cutting blades attached to and radially extending from said shaft, said blades being substantially equally spaced about said shaft.

8. The device as recited in claim 5 wherein said cutting means comprises at least one cautery attached to and radially extending from said shaft.

9. The device as recited in claim 1 further comprising an inflatable balloon mounted on said shaft, said balloon being in fluid communication with a balloon inflation means.

10. The device as recited in claim 5 wherein said sheath has a wall thickness which increases at said distal end to prevent deformation and splaying of said distal end during insertion and placement of said device.

11. An insertable catheter device for incising a stenosis in an artery, said device usable in conjunction with a standard guide wire, said device comprising:

a shaft member formed with a lumen sized to receive said guide wire, said shaft member being longitudinally movable from a remote location;

a hollow catheter sheath selectively covering said shaft member, said catheter sheath having a distal end forming an opening, said opening allowing said shaft member to exit said sheath;

cutting means attached to said shaft member for making longitudinal incisions in said stenosis when said shaft member is moved relative to said sheath from a covered position to an extended position; and guide means formed in said catheter sheath and engaged by said shaft member for controlling the alignment and magnitude of travel of said shaft member relative to said catheter sheath during movement by said shaft member.

12. The device as recited in claim 11 wherein said cutting member further comprises a plurality of alignment lugs radially extending from and attached to said shaft member proximally of said cutting means, said alignment lugs slidingly engaging said guide means to prevent rotation of said shaft member relative to said catheter sheath and to limit lengths of said longitudinal incisions during said movement of said shaft member.

13. The device as recited in claim 12 wherein said guide means is a plurality of longitudinal slots formed by said catheter sheath.

14. The device as recited in claim 13 wherein said cutting means comprises at least one cutting blade attached to and radially extending from said shaft member.

15. The device as recited in claim 14 wherein said cutting means comprises a plurality of cutting blades attached to and radially extending from said shaft member, said blades being substantially equally spaced about said shaft member.

16. The device as recited in claim 13 wherein said cutting means comprises at least one cautery attached to and radially extending from said shaft member.

17. The device as recited in claim 11 wherein said shaft includes at least one flexible member allowing said shaft to flex.

18. The device as recited in claim 11 further comprising an inflatable balloon mounted on said shaft member, said balloon being in fluid communication with an inflation means.

19. An insertable catheter device for longitudinally incising a stenosis in an artery, said device comprising:

a shaft member including a flexible section, said flexible section is a spring member allowing flexing of said shaft member, said shaft member being longitudinally movable from a remote location;

a hollow catheter sheath selectively covering said shaft member, said catheter sheath having a distal end forming an opening, said opening allowing said shaft member to exit said sheath; and cutting means attached to said shaft member for making longitudinal incisions in said stenosis when said shaft member is moved relative to said sheath from a covered position to an extended position.

20. A method of reducing the flow restriction resulting from a stenosis in an artery comprising the steps of:

inserting a guide wire in an artery of a being and moving said guide wire along said artery until said guide wire has passed said arterial stenosis;

placing a catheter device on said wire, said catheter device comprising a shaft member formed with a lumen sized to receive said guide wire, said shaft member being longitudinally movable from a remote location, a hollow catheter sheath selectively covering said shaft member, said catheter sheath having a distal end forming an opening, said opening allowing said shaft member to exit said sheath, a cutting means attached to said shaft member for making longitudinal incisions in said stenosis when said shaft member is moved relative to said sheath from a covered position to an extended position, and a guide means formed in said catheter sheath and engaged by said shaft member for controlling the alignment and magnitude of travel of said shaft member relative to said catheter sheath during movement by said shaft member;

moving said catheter device along said wire until said catheter device is adjacent said arterial stenosis;

extending and retracting said shaft member such that said cutting means longitudinally incises said stenosis; and removing said catheter device and said guide wire from said artery.

21. The method as recited in claim 20 further comprising rotating said catheter after said extending and retracting step and repeating said extending and retracting step.

22. The method as recited in claim 20 further comprising the steps of positioning an inflatable balloon on said shaft member in said arterial stenosis, inflating said balloon, and deflating said balloon prior to removing said catheter from said artery.

23. The method as recited in claim 20 further comprising the steps of placing an inflatable balloon catheter on said guide wire after removal of said catheter device from said artery and prior to removal said guide wire, positioning said balloon catheter in said stenosis, inflating and deflating a balloon attached to said balloon catheter, and removing said balloon catheter from said artery.

* * * * *